(12) United States Patent
Hsu et al.

(10) Patent No.: US 8,211,909 B2
(45) Date of Patent: *Jul. 3, 2012

(54) TREATMENT OF ANTIBIOTIC-RESISTANT BACTERIA INFECTION

(75) Inventors: Ming-Chu Hsu, Glendora, CA (US); Chi-Hsin Richard King, Holladay, UT (US); Shu-Jen Chen, Taipei (TW); Luke Lin, Singapore (SG)

(73) Assignee: TaiGen Biotechnology Co., Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/206,060

(22) Filed: Sep. 8, 2008

(65) Prior Publication Data

US 2010/0004282 A1 Jan. 7, 2010

Related U.S. Application Data

(60) Provisional application No. 61/077,293, filed on Jul. 1, 2008.

(51) Int. Cl.
*A61K 31/47* (2006.01)
(52) U.S. Cl. .................................... 514/312
(58) Field of Classification Search .............. 514/312
See application file for complete search history.

(56) References Cited

U.S. PATENT DOCUMENTS

| | | | |
|---|---|---|---|
| 6,329,391 B1 * | 12/2001 | Ledoussal et al. | 514/312 |
| 2002/0173501 A1 | 11/2002 | Ledoussal et al. | |
| 2004/0038975 A1 | 2/2004 | Ledoussal et al. | |
| 2005/0096278 A1 | 5/2005 | Ellsworth | |
| 2006/0100436 A1 | 5/2006 | Ledoussal et al. | |
| 2007/0232650 A1 | 10/2007 | Redman-Furey et al. | |
| 2007/0232804 A1 | 10/2007 | Reilly | |
| 2009/0111851 A1 | 4/2009 | Ledoussal et al. | |

FOREIGN PATENT DOCUMENTS

| | | |
|---|---|---|
| WO | WO99/14214 | 3/1999 |
| WO | WO99/35117 | 7/1999 |
| WO | WO02/48113 | 6/2002 |
| WO | WO2004/013103 | 2/2004 |
| WO | WO2007/110834 | 10/2007 |
| WO | WO2007/110835 | 10/2007 |
| WO | WO2007/110836 | 10/2007 |
| WO | WO2007-110836 | 10/2007 |
| WO | 2009/023473 | 2/2009 |
| WO | 2010/009014 | 1/2010 |

OTHER PUBLICATIONS

Shopsin et al (Int J Antimicrob Agents 24:32-34, 2004).*
Joseph et al (Podiatry Today, vol. 18, 2005).*
Waterer GW, Wunderink RG. The influence of the severity of community-acquired pneumonia on the usefulness of blood cultures; Respir. Med. Jan. 2001; 95(1): 78-82.
"TaiGen Initiates Phase II Trial of Nemonoxacin for Treatment of Adult Community Acquired Pneumonia (CAP)", Jan. 8, 2007, retrieved from Internet May 14, 2008, 2 pages.
Anonymous: "TaiGen Initiates Phase IB Trial of a Novel Quinolone Antibiotic", Jun. 18, 2005, pp. 1-2, XP007919904.
Anonymous: "TaiGen Announces Positive Data From the Phase II Study of Nemonoxacin (TG-873870) in Community-Acquired Pneumonia", Apr. 7, 2008, p. 1, XP007919900, http://www.taigenbiotech.com/news.html.
A. Arjona et al: "Nemonoxacin", Drugs of the Future, vol. 34, No. 3, Jan. 1, 2009, p. 196, XP55014485.

* cited by examiner

*Primary Examiner* — Craig Ricci
(74) *Attorney, Agent, or Firm* — Occhiuti Rohlicek & Tsao LLP

(57) ABSTRACT

This invention relates to a method of treating infection by methicillin-nonsusceptibale bacteria, vancomycin-nonsusceptibale bacteria, penicillin-nonsusceptibale bacteria, clarithromycin-nonsusceptibale bacteria, or metronidazole-nonsusceptibale bacteria by administering to a subject in need thereof an effective amount of a compound of the following formula:

12 Claims, No Drawings

TREATMENT OF ANTIBIOTIC-RESISTANT BACTERIA INFECTION

CROSS REFERENCE

This application claims priority to U.S. Provisional Application Ser. No. 61/077,293, filed Jul. 1, 2008, the contents of which are incorporated herein by reference.

BACKGROUND OF THE INVENTION

Antibiotic resistance in bacteria may be an inherent trait or may be acquired by mutation. Bacteria that are resistant to antibiotics become a serious public health threat.

For example, approximately 1% of the population in the world has methicillin-resistant *staphylococcus aureus* (MRSA), a bacterial strain that is resistant to commonly used antibiotics. Most MRSA infections occur in hospitals and healthcare facilities, such as nursing homes and dialysis centers. It is known as heath-associated MRSA (HA-MRSA). Elderly people or people with weakened immune systems are at a high risk of HA-MRSA infection. Recently, among otherwise healthy people in a wider community, another type of MRSA, community-associated MRSA (CA-MRSA), has been found. CA-MRSA is responsible for serious skin and soft tissue infections and for a serious form of pneumonia.

Infection caused by antibiotic-resistant bacteria is often incurable by existing antibiotics. Thus, there is a need to develop new antibiotic drugs.

SUMMARY

This invention relates to a method of treating infection caused by methicillin-nonsusceptibale bacteria, vancomycin-nonsusceptibale bacteria, penicillin-nonsusceptibale bacteria, clarithromycin-nonsusceptibale bacteria, or metronidazole-nonsusceptibale bacteria. The method includes administering to a subject an effective amount of one of the quinolone compounds of formula (I):

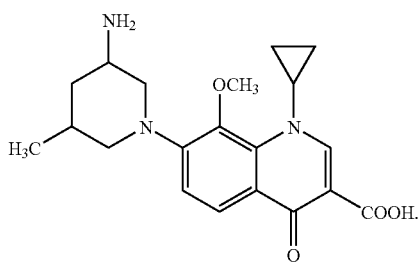

formula (I)

The above quinolone compounds contain asymmetric centers. They include all forms of stereoisomers. Two examples of isomeric compounds are:

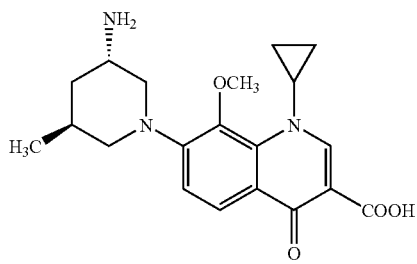

(3S,5S)-7-[3-amino-5-methyl-piperidinyl]-1-cyclopropyl-1,4-dihydro-8-methoxy-4-oxo-3-quinolinecarboxylic acid

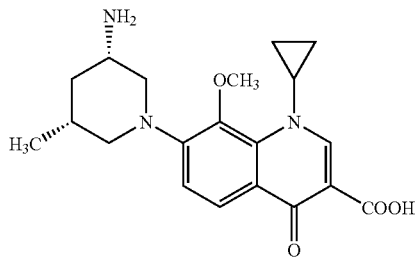

(3S,5R)-7-[3-amino-5-methyl-piperidinyl]-1-cyclopropyl-1,4-dihydro-8-methoxy-4-oxo-3-quinolinecarboxylic acid The quinolone compounds can be the compounds themselves, as well as their salts, prodrugs, or solvates. A salt can be formed between an anion and a positively charged group (e.g., amino) on a compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on the compound. Suitable cations include sodium ion, potassium ion, magnesium ion, calcium ion, and an ammonium cation such as tetramethylammonium ion. A prodrug can be ester and another pharmaceutically acceptable derivative, which, upon administration to a subject, is capable of providing a compound of formula (I). A solvate refers to a complex formed between a compound of formula (I) and a pharmaceutically acceptable solvent. A pharmaceutically acceptable solvent can be water, ethanol, isopropanol, ethyl acetate, acetic acid, and ethanolamine. The quinolone compounds used to practice this invention can therefore be, for example, malate salts (malic acid salts) of the compounds and hemihydrates of the salts.

Also within the scope of this invention is a composition containing one or more of the above-described quinolone compounds and a pharmaceutically acceptable carrier for use in treating infection caused by methicillin-nonsusceptibale bacteria, vancomycin-nonsusceptibale bacteria, penicillin-nonsusceptibale bacteria, clarithromycin-nonsusceptibale bacteria, or metronidazole-nonsusceptibale bacteria, as well as the use of such a composition for the manufacture of a medicament for treating the infection. The bacteria mentioned above can be methicillin-resistant *Staphylococcus*

*aureus*, efflux-related methicillin-resistant *Staphylococcus aureus*, vancomycin-intermediate *Staphylococcus aureus*, hetero-vancomycin-intermediate *Staphylococcus aureus*, or vancomycin-resistant *Staphylococcus aureus*. Examples of infection caused by the just-mentioned bacteria include, but are not limited to, surgical wound infection, urinary tract infection, bloodstream infection (sepsis), pneumonia (hospital-acquired or community-acquired), diabetic foot infection, and skin infection such as cellulites, boils, abscesses, sty, carbuncles, and impetigo.

Details of several embodiments of the invention are set forth in the description below. Other features, objects, and advantages of the invention will be apparent from the description, and also from the claims.

DETAILED DESCRIPTION

The quinolone compounds used to practice this invention contain can be synthesized by conventional methods. Example 1 below illustrates synthetic methods to prepare two isomeric compounds. A skilled person would be able to obtain other isomers or other forms of the compounds by modifying the synthesis. Synthetic chemistry transformations and protecting group methodologies (protection and deprotection) useful in the synthesis are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds thus synthesized can be further purified by flash column chromatography, high performance liquid chromatography, crystallization, or any other suitable methods.

The above-described quinolone compounds inhibit growth of methicillin-nonsusceptibale bacteria, vancomycin-nonsusceptibale bacteria, penicillin-nonsusceptibale bacteria, clarithromycin-nonsusceptibale bacteria, and metronidazole-nonsusceptibale bacteria. Thus, an aspect of this invention relates to a method of treating infection caused by one of the bacteria by administering to a subject in need thereof an effective amount of one of the quinolone compounds. An embodiment of this method is use of a quinolone compound to treat infection caused by multi-resistant *Streptococcus pneumoniae*, in which the bacteria are resistant to at least one of methicillin, vancomycin, and penicillin.

The term "nonsusceptible" used herein refers to resistance to a drug at the intermediate level through the full level. Methicillin-nonsusceptible bacteria include, but are not limited to, methicillin-resistant *Staphylococcus aureus*, efflux-related methicillin-resistant *Staphylococcus aureus*, community-associated methicillin-resistant *Staphylococcus aureus*, and methicillin-resistant *Staphylococcus epidermidis*. Vancomycin-nonsusceptible bacteria include, but are not limited to, hetero-vancomycin-intermediate *Staphylococcus aureus*, vancomycin-intermediate *Staphylococcus aureus*, and vancomycin-resistant *Staphylococcus aureus*. Penicillin-nonsusceptible bacteria include, but are not limited to, penicillin-resistant *Streptococcus pneumoniae*. Clarithromycin-nonsusceptible bacteria include, but are not limited to, clarithromycin-resistant *Helicobacter pylori*. Metronidazole-nonsusceptible bacteria include, but are not limited to, metronidazole-resistant *Helicobacter pylori*.

The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents. The term "treating" refers to administering one of the above-described quinolone compounds to a subject that has the above-mentioned infection, or has a symptom of such infection, or has a predisposition toward such infection, with the purpose to cure, heal, alleviate, relieve, alter, remedy, ameliorate, improve, or affect the infection, the symptoms of the infection, or the predisposition toward the infection.

To practice this method, the quinolone compounds can be administered orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762. . Creams are preferably formulated from a mixture of mineral oil, self-emulsifying beeswax and water in which mixture the active ingredient, dissolved in a small amount of oil, such as almond oil, is admixed. An example of such a cream is one which includes about 40 parts water, about 20 parts beeswax, about 40 parts mineral oil and about 1 part almond oil. Mixing a solution of the active ingredient in vegetable oil, such as almond oil, with warm soft paraffin and allowing the mixture to cool may formulate ointments. An example of such an ointment is one, which includes about 30% almond and about 70% white soft paraffin by weight.

A carrier in a pharmaceutical composition must be "acceptable" in the sense that it is compatible with active ingredients of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active ingredients. Examples of other carriers include colloidal silicon dioxide, magnesium stearate, cellulose, sodium lauryl sulfate, and D&C Yellow #10.

Suitable in vitro assays can be used to preliminarily evaluate the efficacy of one of the above-described compounds in inhibiting growth of bacteria. The compound can further be examined for its efficacy in treating bacterial infection by in vivo assays. For example, the compound can be administered to an animal (e.g., a mouse model) having infection and its therapeutic effects are then accessed. Based on the results, an appropriate dosage range and administration route can also be determined.

Without further elaboration, it is believed that the above description has adequately enabled the present invention. The following specific examples are, therefore, to be construed as merely illustrative, and not limitative of the remainder of the disclosure in any way whatsoever. All of the publications, including patents, cited herein are hereby incorporated by reference in their entirety.

EXAMPLE 1

Malate salts of (3S,5S)-7-[3-amino-5-methyl-piperidinyl]-1-cyclopropyl-1,4-dihydro-8-methoxy-4-oxo-3-quinolinecarboxylic acid (Compound 1) and (3S,5R)-7-[3-amino-5-methyl-piperidinyl]-1-cyclopropyl-1,4-dihydro-8-methoxy-4-oxo-3-quinolinecarboxylic acid (Compound 1') were synthesized as follows:

(A) Synthesis of (3S,5S)-(5-Methyl-piperidin-3-yl)-carbamic acid tert-butyl ester (Compound 9) and (3S,5R)-(5-Methyl-piperidin-3-yl)-carbamic acid tert-butyl ester (Compound 9')

Compound 9' was synthesized as shown in Scheme 1 below:

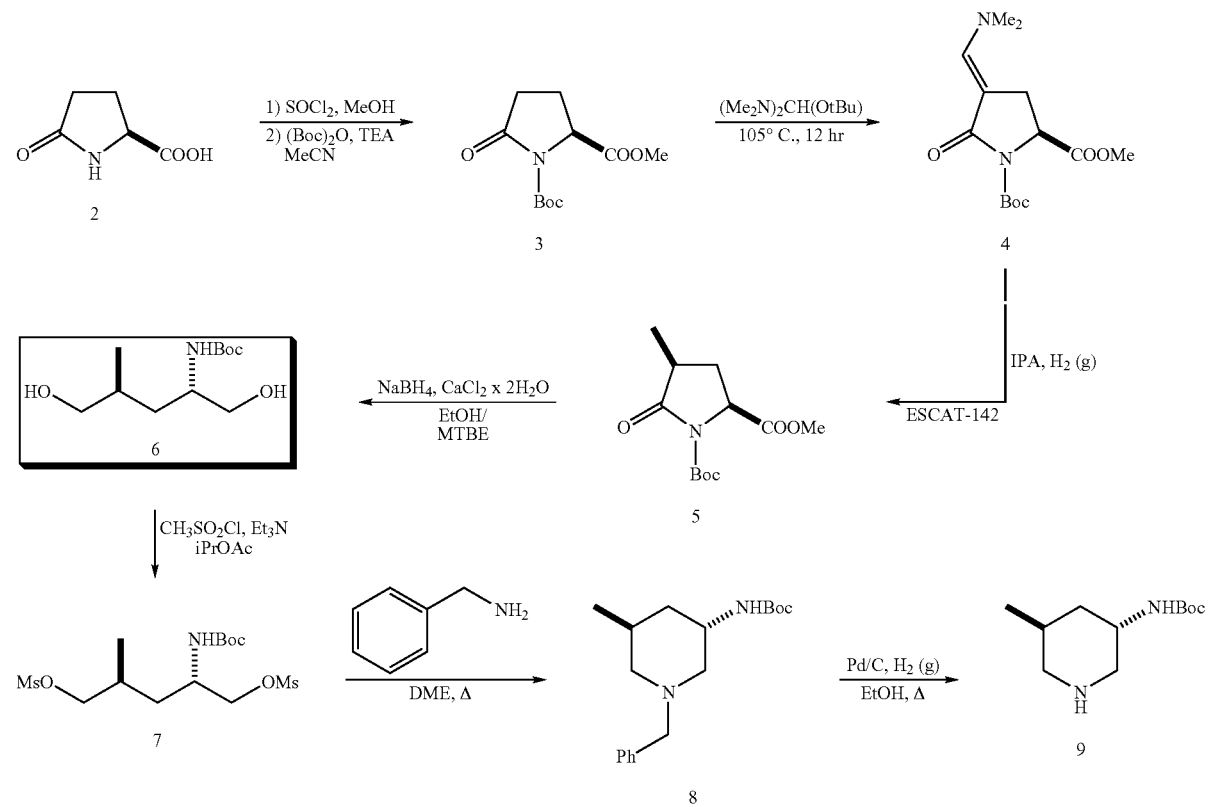

A 50-L reactor was charged with Compound 2 (5.50 kg, 42.60 mol), methanol (27 L) and cooled to 10-15° C. Thionyl chloride (10.11 kg, 2.0 equiv.) was added via an addition funnel over a period of 65 min, with external cooling to keep temperature below 30°. The resulting solution was stirred at 25° C. for 1.0 hour, after which methanol was removed under reduced pressure. The oily residue was azeotroped with ethyl acetate (3×2.5 L) to remove residual methanol, dissolved in ethyl acetate (27.4 L), charged into a 50 L reactor, and neutralized by slow addition of triethylamine (3.6 kg) below 30° C. The resulting suspension was filtered to remove triethylamine hydrochloride.

The filtrate was charged to a 50 L reactor, along with DMAP (0.53 kg). Di-tert-butyl dicarbonate (8.43 kg) was added via hot water heated addition funnel, over a period of 30 min at a temperature of 20-30° C. The reaction was complete after 1 hour as determined by TLC analysis. The organic phase was washed with ice cold 1N HCl (2×7.5 L), saturated sodium bicarbonate solution (1×7.5 L), dried over magnesium sulfate, and filtered. After ethyl acetate was removed under reduced pressure, crystalline slurry was obtained, triturated with MTBE (10.0 L), and filtered to afford Compound 3 as a white solid (5.45 kg, 52.4%).

Anal. Calcd for $C_{11}H_{17}NO_5$: C, 54.3; H, 7.04; N, 5.76. Found: C, 54.5; H, 6.96; N, 5.80. HRMS (ESI$^+$) Expected for $C_{11}H_{18}NO_5$, [M+H] 244.1185. Found 244.1174; $^1$H NMR (CDCl$_3$, 500 MHz): δ=4.54 (dd, J=3.1, 9.5 Hz, 1H), 3.7 (s, 3H), 2.58-2.50 (m, 1H), 2.41 (ddd, 1H, J=17.6, 9.5, 3.7), 2.30-2.23 (m, 1H), 1.98-1.93 (m, 1H), 1.40 (s, 9H); $^{13}$C NMR (CDCl$_3$, 125.70 MHz) δ 173.3, 171.9, 149.2, 83.5, 58.8, 52.5, 31.1, 27.9, 21.5. Mp 70.2° C.

A 50-L reactor was charged with Compound 3 (7.25 kg, 28.8 mol), DME (6.31 kg), and Bredereck's Reagent (7.7 kg, 44.2 mole). The solution was agitated and heated to 75° C.±5° C. for three hours. The reaction was cooled to 0° C. over an hour, during which time a precipitate formed. The mixture was kept at 0° C. for an hour, filtered, and dried in a vacuum oven for at least 30 hours at 30° C.±5° C. to give compound 4 as a white crystalline solid (6.93 kg, 77.9%).

Anal. Calcd for $C_{14}H_{22}N_2O_5$: C, 56.4; H, 7.43; N, 9.39. Found C, 56.4; H, 7.32; N, 9.48; HRMS (ESI$^+$) Expected for $C_{14}H_{22}N_2O_5$, [M+H] 299.1607. Found 299.1613; $^1$H NMR (CDCl$_3$, 499.8 MHz) δ=7.11 (s, 1H), 4.54 (dd, 1H, J=10.8, 3.6), 3.74 (s, 3H), 3.28-3.19 (m, 1H), 3.00 (s, 6H), 2.97-2.85 (m,1H), 1.48 (s, 9H); $^{13}$C NMR (CDCl$_3$, 125.7 MHz) δ=172.6, 169.5, 150.5, 146.5, 90.8, 82.2, 56.0, 52.3, 42.0, 28.1, 26.3. MP 127.9° C.

A 10-gallon Pfaudler reactor was charged with ESCAT 142 (Engelhard Corp. N.J, US) 5% palladium powder on carbon (50% wet, 0.58 kg wet wt.), Compound 4 (1.89 kg, 6.33 mol), and isopropanol (22.4 Kg). After agitated under a 45-psi hydrogen atmosphere at 45° C. for 18 hrs, the reaction mixture was cooled to room temperature and filtered though a bed of Celite (0.51 kg). The filtrate was evaporated under reduced pressure to give a thick oil, which was solidified on standing to afford Compound 5 (1.69 kg, 100%) as a 93:7 diastereomeric mixture.

A sample of product mixture was purified by preparative HPLC to give material for analytical data. Anal. Calcd for $C_{12}H_{19}NO_5$: C, 56.0; H, 7.44; N, 5.44. Found C, 55.8; H, 7.31; N, 5.44; MS (ESI$^+$) Expected for $C_{12}H_{19}NO_5$, [M+H] 258.1342. Found 258.1321; $^1$H NMR (CDCl$_3$, 499.8 MHz) δ=4.44 (m, 1H), 3.72 (s, 3H), 2.60-2.48 (m, 2H), 1.59-1.54 (m, 1H), 1.43 (s, 9H), 1.20 (d, j=6.8 Hz,3H); $^{13}$C NMR (CDCl$_3$, 125.7 MHz) δ=175.7, 172.1, 149.5, 83.6, 57.4, 52.5, 37.5, 29.8, 27.9, 16.2. Mp 89.9° C.

A 50-L reactor was charged with Compound 5 (3.02 kg, 11.7 mol), absolute ethanol (8.22 kg), and MTBE (14.81 kg). Sodium borohydride (1.36 kg, 35.9 mol) was added in small portions at 0° C.±5° C. A small amount of effervescence was observed. The reaction mixture was warmed to 10° C.±5° C. and calcium chloride dihydrate (2.65 kg) was added in portions at 10° C.±5° C. over an hour. The reaction was allowed to warm to 20° C.±5° C. over one hour and agitated for an additional 12 hours at 20° C.±5° C. After the reaction was cooled to −5° C.±5° C., ice-cold 2N HCl (26.9 kg) was added slowly at of 0° C.±5° C. Agitation was stopped. The lower aqueous phase was removed. The reactor was charged with aqueous saturated sodium bicarbonate (15.6 kg) over five minutes under agitation. Agitation was stopped again and the lower aqueous phase was removed. The reactor was charged with magnesium sulfate (2.5 kg) and agitated for at least 10 minutes. The mixture was filtered though a nutsche filter, and concentrated under reduced pressure to afford Compound 6 (1.80 kg, 66%).

Anal. Calcd for $C_{11}H_{23}NO_4$: C, 56.6 H, 9.94; N, 6.00. Found C, 56.0; H, 9.68; N, 5.96; HRMS (ESI$^+$) Expected for $C_{11}H_{24}NO_4$, [M+H] 234.1705. Found 234.1703; $^1$H NMR (CDCl$_3$, 500 MHz) δ=6.34 (d, J=8.9 Hz, 1H, NH), 4.51 (t, J=5.8, 5.3 Hz, 1H, NHCHCH$_2$OH), 4.34 (t, J=5.3, $\overline{5.3}$ Hz, 1H, CH3CHCH$_2$OH), 3.46-3.45, ($\overline{m}$, 1H, NHCH), 3.28 (dd, J=10.6, 5.3 H$\overline{z,}$ NHCHCHHOH), 3.21 (dd, J$\overline{=}$10.2, 5.8 Hz, 1H, CH$_3$CHCHHOH), $\overline{3}$.16 (dd, J=10.2, 6.2 Hz, 1H, NHCHCHH$\overline{OH}$), 3.12 (dd, J=10.6, 7.1 Hz, 1H, CH$_3$CHCH HOH), 1.5$\overline{3}$-1.50 (m, 1H, CH$_3$CHCHHOH), 1.35 (s, 9H, O(C $\overline{H}_3)_3$, 1.30 (ddd, J=13.9, 10.2, 3.$\overline{7}$ Hz, 1H, NHCHCHHCH), $\overline{1}$.14 (ddd, J=13.6, 10.2, 3.4 Hz, 1H, NHCHCHHCH$\overline{)}$, 0.80 (d, J=6.6 Hz, 3H, CH$_3$); $^{13}$C NMR (CDCl$_3$, $\overline{125}$.7 MHz) δ 156.1, 77.9, 50.8, 65.1, 67.6, 65.1, 35.6, 32.8, 29.0, 17.1. Mp 92.1° C.

A 50 L reactor was charged with a solution of Compound 6 (5.1 kg) in isopropyl acetate (19.7 kg). The reaction was cooled to 15° C.±5° C. and triethylamine (7.8 kg) was added at that temperature. The reactor was further cooled to 0° C.±5° C. and methanesulfonyl chloride (MsCl) (6.6 kg) was added. The reaction was stirred for a few hours and monitored for completion by HPLC or TLC. The reaction was quenched by saturated aqueous bicarbonate solution. The organic phase was isolated and washed successively with cold 10% aqueous triethylamine solution, cold aqueous HCl solution, cold saturated aqueous bicarbonate solution, and finally saturated aqueous brine solution. The organic phase was dried, filtered, and concentrated in vacuo below 55° C.±5° C. to afford compound 7 as a solid/liquid slurry, which was used in the subsequent reaction without further purification.

After charged with 9.1 kg of neat benzylamine, a 50 L reactor was warmed to 55° C., at which temperature, a solution of compound 7 (8.2 kg) in 1,2-dimethoxyethane (14.1 kg) was added. After the addition, the reaction was stirred at 60° C.±5° C. for several hours and monitored for completion by TLC or HPLC. The reaction was cooled to ambient temperature and the solvent was removed under vacuum. The residue was diluted with 11.7 kg of 15% (v/v) ethyl acetate/ hexanes solution and treated, while agitating, with 18.7 kg of 20% (wt) aqueous potassium carbonate solution. A triphasic mixture was obtained upon standing. The upper organic layer was collected. The isolated middle layer was extracted twice again with 11.7 kg portions of 15% (v/v) ethyl acetate/hexanes solution. The combined organic layers were concentrated under vacuum to give an oily residue. The residue was then purified by chromatography to afford Compound 8 as an oil.

A 40 L pressure vessel was charged with 0.6 kg 50% wet, solid palladium on carbon (E101, 10 wt. %) under flow of nitrogen. A solution of Compound 8 (3.2 kg) in 13.7 kg of absolute ethanol was then added to the reactor under nitrogen. The reactor was purged with nitrogen and then pressurized with hydrogen at 45 psi. The reaction was then heated to 45° C. It was monitored by TLC or LC. Upon completion, the reaction was cooled to ambient temperature, vented, and purged with nitrogen. The mixture was filtered through a bed of Celite and the solid was washed with 2.8 kg of absolute ethanol. The filtrate was concentrated under vacuum to afford Compound 9 as a waxy solid.

TLC $R_f$ (Silica $F_{254}$, 70:30 v/v ethyl acetate-hexanes, KMnO$_4$ stain)=0.12; $^1$H NMR (300 MHz, CDCl$_3$) δ 5.31 (br s, 1H), 3.80-3.68 (m, 1H), 2.92 (d, J=11.4 Hz, 1H), 2.77 (AB quart, J$_{AB}$=12.0 Hz, v=50.2 Hz, 2H), 2.19 (t, J=10.7 Hz, 1H), 1.82-1.68 (m, 2H), 1.54 (br s, 1H), 1.43 (s, 9H), 1.25-1.15 (m, 1H), 0.83 (d, J=6.6 Hz, 3H); $^{13}$C NMR (75 MHz, CDCl$_3$) δ: 155.3, 78.9, 54.3, 50.8, 45.3, 37.9, 28.4, 27.1, 19.2; MS (ESI+) m/z 215 (M+H), 429 (2M+H).

Similarly, (3S,5R)-(5-Methyl-piperidin-3-yl)-carbamic acid tert-butyl ester (Compound 9') was synthesized as shown in Scheme 2.

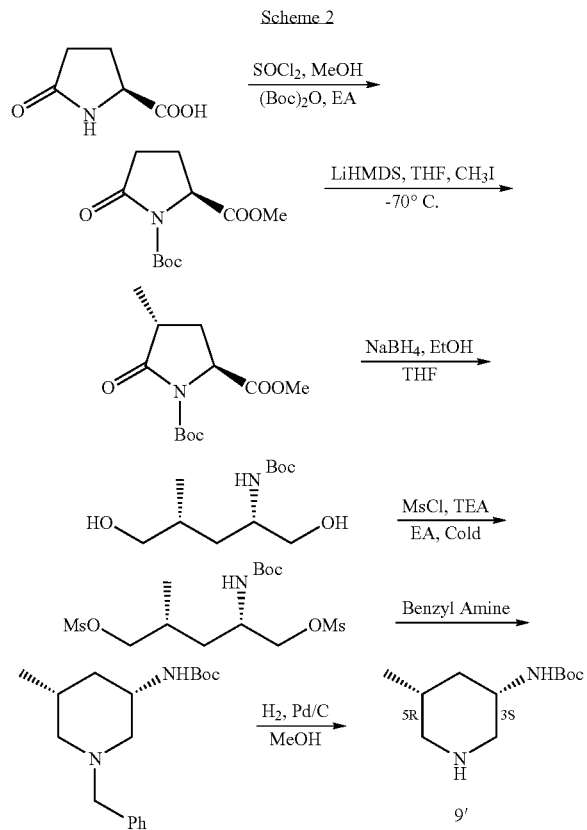

(B) Synthesis of 1-Cyclopropyl-7-fluoro-8-methoxy-4-oxo-1,4-dihydro-quinoline-3-carboxylic acid (Compound 10)

Compound 10 was prepared according to the method described in U.S. Pat. No. 6,329,391.

(C) Synthesis of borone ester chelate of 1-Cyclopropyl-7-fluoro-8-methoxy-4-oxo-1,4-dihydro-quinoline-3-carboxylic acid (Compound 11)

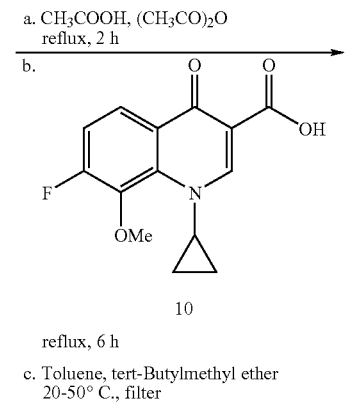

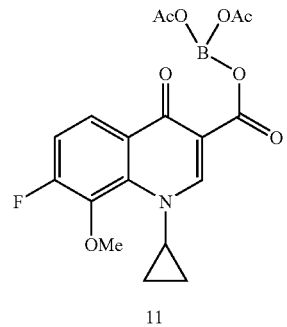

A reactor was charged with boron oxide (2.0 kg, 29 mol), glacial acetic acid (8.1 L, 142 mol), and acetic anhydride (16.2 L, 171 mol). The resulting mixture was refluxed at least 2 hours, and then cooled to 40° C., at which temperature, 7-fluoroquinolone acid compound 10 (14.2 kg, 51 mol) was added. The mixture was refluxed for at least 6 hours, and then cooled to about 90° C. Toluene (45 L) was added to the reaction. At 50° C., tert-butylmethyl ether (19 L) was added to introduce precipitation. The mixture was then cooled to 20° C. and filtered to isolate the precipitation. The isolated solid was then washed with tert-butylmethyl ether (26 L) prior to drying in a vacuum oven at 40° C. (50 torr) to afford Compound 11 in a yield of 86.4%.

Raman (cm$^{-1}$): 3084.7, 3022.3, 2930.8, 1709.2, 1620.8, 1548.5, 1468.0, 1397.7, 1368.3, 1338.5, 1201.5, 955.3, 653.9, 580.7, 552.8, 384.0, 305.8. NMR (CDCl$_3$, 300 MHz) δ (ppm): 9.22 (s, 1H), 8.38-8.33 (m, 1H), 7.54 (t, J=9.8 Hz, 1H), 4.38-4.35 (m, 1H), 4.13 (s, 3H), 2.04 (s, 6H), 1.42-1.38 (m, 2H), 1.34-1.29 (m, 2H). TLC (Whatman MKC18F Silica, 60 Å, 200 μm), Mobile Phase: 1:1 (v/v) CH$_3$CN: 0.5N NaCl (aq), UV (254/366 nm) visualization; R$_f$=0.4-0.5.

(D) Synthesis of Malate Salt of (3S,5S)-7-[3-amino-5-methyl-piperidinyl]-1-cyclopropyl-1,4-dihydro-8-methoxy-4-oxo-3-quinolinecarboxylic acid (Compound 1) and malate salt of (3S,5R)-7-[3-amino-5-methyl-piperidinyl]-1-cyclopropyl-1,4-dihydro-8-methoxy-4-oxo-3-quinolinecarboxylic acid (Compound 1')

Compound 1 was synthesized from compound 9 as shown in Scheme 4 below:

A reactor was charged with Compound 11 (4.4 kg, 10.9 mol), Compound 9 (2.1 kg, 9.8 mol), triethylamine (TEA) (2.1 L, 14.8 mol), and acetonitrile (33.5 L, 15.7 L/kg). The resulting mixture was stirred at approximately 50° C. till completion of the reaction, as monitored by HPLC or reverse phase TLC. It was cooled to approximately 35° C. and the reaction volume was reduced to approximately half by distillation of acetonitrile under vacuum between 0-400 torr. After 28.2 kg of 3.0 N NaOH (aq) solution was added, the reaction mixture was warmed to approximately 40° C., distilled under

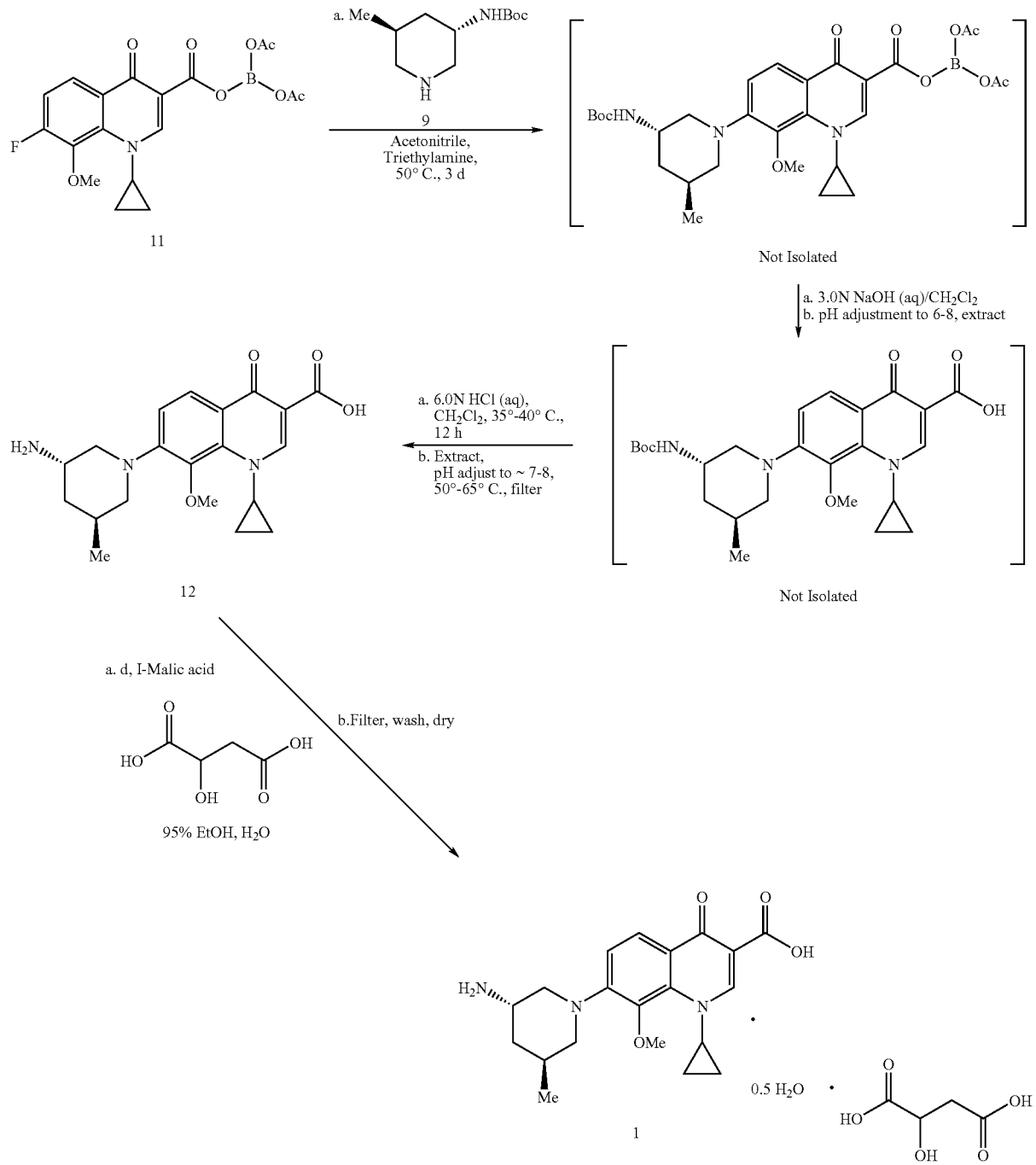

vacuum until no further distillates were observed, and hydrolyzed at room temperature. Upon completion of hydrolysis, which was monitored by HPLC or reverse phase TLC, 4-5 kg of glacial acetic acid was added to neutralize the reaction mixture.

The resulting solution was extracted 3 times with 12.7 kg (9.6 L) of dichloromethane. The organic layers were combined and transferred to another reactor. The reaction volume was reduced to approximately a half by evaporation at 40° C. After 20.2 Kg 6.0N HCl (aq) solution was added, the reaction mixture was stirred for at least 12 hours at 35° C. After the reaction was completed as monitored by HPLC or reverse phase TLC, agitation was discontinued to allow phase separation. The organic phase was removed and the aqueous layer was extracted with 12.7 kg (9.6 L) of dichloromethane. The aqueous layer was diluted with 18.3 kg distilled water and warmed to approximately 50° C. Dichloromethane was further removed by distillation under vacuum (100-400 torr).

The pH of the aqueous solution was then adjusted to 7.8-8.1 by adding about 9.42 kg of 3.0 N NaOH (aq) below 65° C. The reaction mixture was stirred at 50° C. for at least an hour and then cooled to room temperature. The precipitate was isolated by suction filtration, washed twice with 5.2 kg of distilled water, and dried with suction for at least 12 hours and then in a convection oven at 55° C. for additional 12 hours. Compound 12 (3.2 kg, 79%) was obtained as a solid.

A reactor was charged with 3.2 kg of Compound 12 and 25.6 kg of 95% ethanol. To the reactor was added 1.1 kg of solid D,L-malic acid. The mixture was refluxed temperature (~80° C.). Distilled water (~5.7 L) was added to dissolve the precipice and 0.2 kg of activated charcoal was added. The reaction mixture was passed through a filter. The clear filtrate was cooled to 45° C. and allowed to sit for at least 2 hours to allow crystallization. After the reaction mixture was further cooled to 5° C., the precipitate was isolated by suction filtration, washed with 6.6 kg of 95% ethanol, and dried with suction for at least 4 hours. The solid was further dried in a convection oven at 45° C. for at least 12 hours to afford 3.1 kg of Compound 1 (yield: 70%).

NMR (D$_2$O, 300 MHz) δ (ppm): 8.54 (s, 1H), 7.37 (d, J=9.0 Hz, 1H), 7.05 (d, J=9.0 Hz, 1H), 4.23-4.18 (m, 1H), 4.10-3.89 (m, 1H), 3.66 (br s, 1H), 3.58 (s, 3H), 3.45 (d, J=9.0 Hz, 1H), 3.34 (d, J=9.3 Hz, 1H), 3.16 (d, J=12.9 Hz, 1H), 2.65 (dd, J=16.1, 4.1 Hz, 1H), 2.64-2.53 (m, 1H), 2.46 (dd, J=16.1, 8.0 Hz, 1H), 2.06 (br s, 1H), 1.87 (d, J=14.4 Hz, 1H), 1.58-1.45 (m, 1H), 1.15-0.95 (m, 2H), 0.91 (d, J=6.3 Hz, 3H), 0.85-0.78 (m, 2H).

Similarly, Compound 1' was synthesized from Compound 9' as shown in Scheme 5 below:

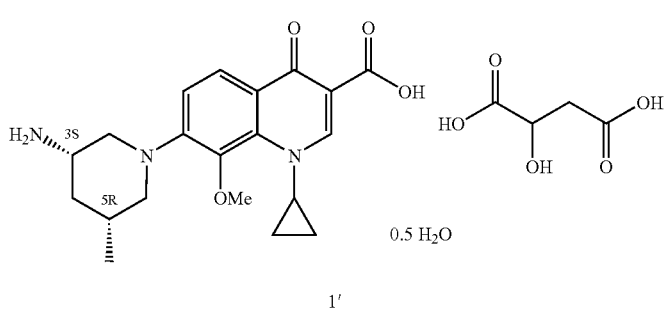
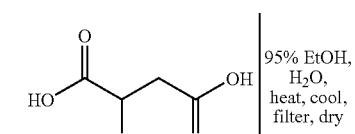

EXAMPLE 2

Inhibition of Methicillin-resistant *Staphylococcus aureus* (MRSA) by Compound 1

MRSA isolates (n=193) were obtained as part of the Canadian National Intensive Care Unit (CAN-ICU) Study. 19 medical centers from all regions of Canada with active ICUs participated in the CAN-ICU study included. They were requested to only obtain "clinically significant" specimens from patients with a presumed infectious disease. Surveillance swabs, eye, ear, nose and throat swabs were excluded. Anaerobic organisms and fungal organisms were also excluded.

From September 2005-June 2006 (inclusive), each center collected a maximum of 300 consecutive pathogens isolated from blood, urine, tissue/wound, and respiratory specimens (one pathogen per cultured site per patient) of ICU patients. These isolates were shipped to the reference laboratory (Health Sciences Centre, Winnipeg, Canada) on Amies charcoal swabs, subcultured in appropriate media, and stocked in skim milk at −80° C.

The isolates' Methicillin resistance was confirmed using the disk diffusion method described by the Clinical and Laboratory Standards Institute. All isolates underwent mecA PCR, as well as molecular characterization (including PVL analysis and fingerprinting), as previously described, to assess whether they were community-associated or healthcare-associated (Christianson et al., *J Clin Microbiol*. 2007, 45 (6): 1904-11; Mulvey et al., *J Clin. Microbiol.* 2001, 39(10): 3481-5; Mulvey et al., *Emerg Infect Dis*. 2005,11(6): 844-50; Oliveira et al., *Antimicrob Agents Chemother.* 2002, 46(7): 2155-61). The isolates were also subtyped using pulsed-field gel electrophoresis (PFGE) following the Canadian standardized protocol as previously described (Mulvey et al., *J Clin Microbiol.* 2001, 39(10): 3481-5). Their PFGE fingerprints thus obtained were analyzed with BioNumerics v3.5 (Applied Maths St. Marten-Latem, Belgium) using a position tolerance of 1.0 and an optimization of 1.0. Strain relatedness was determined as previously described (Tenover et al., 1995). The fingerprints of the isolates were compared to the national MRSA fingerprint database and were grouped into one of 10 Canadian epidemic MRSA (CMRSA-1, CMRSA-2, etc) as previously described (Mulvey et al., *Emerg Infect Dis*. 2005,11(6):844-50). The MRSA isolates belong to genotypes: CMRSA-1 (USA600), CMRSA-2 (USA 100), CMRSA-4 (USA200), CMRSA-7 (USA400, MW2) and CMRSA-10 (USA300).

Compound 1 and other antibiotics were tested for their inhibitory activity against the MRSA isolates using the broth microdilution guidelines as stipulated by the Clinical and Laboratory Standards Institute. The table below shows the minimum inhibitory concentrations (MICs) of Compound 1 and various fluoroquinolone antibiotics for inhibiting the 193 MRSA isolates:

| MRSA (n = 193) | MIC (µg/mL) | | | |
|---|---|---|---|---|
| | $MIC_{50}$ | $MIC_{90}$ | Range Min | Range Max |
| Compound 1 | 4 | >4 | 0.03 | >4 |
| Cefazolin | 128 | >128 | 2 | >128 |
| Ceftriaxone | >64 | >64 | 8 | >64 |
| Ciprofloxacin | >16 | >16 | 0.5 | >16 |
| Clarithromycin | >32 | >32 | 0.25 | >32 |
| Clindamycin | >8 | >8 | ≦0.12 | >8 |
| Daptomycin | 0.25 | 0.5 | 0.25 | 0.5 |
| Levofloxacin | >32 | >32 | 0.25 | >32 |
| Linezolid | 2 | 2 | 0.5 | 4 |
| Meropenem | 16 | >32 | 0.25 | >32 |
| Moxifloxacin | 8 | >16 | ≦0.06 | >16 |
| Tigecycline | 0.25 | 0.5 | 0.12 | 0.5 |
| Trimethoprim-Sulfa | ≦0.12 | 4 | ≦0.12 | 8 |
| Vancomycin | 1 | 1 | 0.5 | 1 |

The table below shows MICs of Compound 1 and fluoroquinone antibiotics for inhibiting community-associated MRSA (CA-MRSA) strains—USA 300 and USA 400—and healthcare-associated MRSA strains—USA 200, USA 600, and USA 100/800.

| Drug | MRSA MIC50/MIC90 (µg/mL) | | | | |
|---|---|---|---|---|---|
| | USA 200 (HA-MRSA) | USA 300 (CA-MRSA) | USA 400 (CA-MRSA) | USA 600 (HA-MRSA) | USA 100/800 (HA-MRSA) |
| Compound 1 | 2/2 | 0.5/0.5 | 0.06/0.06 | 2/2 | 4/>4 |
| Ciprofloxacin | >16/>16 | >16/>16 | 1/1 | >16/>16 | >16/>16 |
| Levofloxacin | 32/>32 | 8/8 | 0.25/0.25 | 32/>32 | >32/>32 |
| Moxifloxacin | 8/8 | 2/2 | 0.06/0.06 | 8/8 | 16/>16 |
| Vancomycin | 0.5/0.5 | 0.5/0.5 | 1/1 | 1/1 | 1/1 |

-continued

| Drug | MRSA MIC50/MIC90 (µg/mL) | | | | |
| --- | --- | --- | --- | --- | --- |
| | USA 200 (HA-MRSA) | USA 300 (CA-MRSA) | USA 400 (CA-MRSA) | USA 600 (HA-MRSA) | USA 100/800 (HA-MRSA) |
| Linezolid | 2/2 | 1/2 | 2/2 | 2/2 | 2/2 |
| Tigecycline | 0.5/0.5 | 0.25/0.5 | 0.25/0.25 | 0.25/0.5 | 0.25/0.25 |

Compound 1 effectively inhibited MRSA. It was also found that this compound was more active against community-associated-MRSA strains than healthcare-associated-MRSA strains.

Inhibition of Multidrug-Resistant Methicillin-Resistant *Staphylococcus aureus,* and *Enterococci faecium,* and *Enterococci faecalis* by Compound 1

Compound 1 was tested for its inhibitory effect against multidrug-resistant Methicillin-resistant *Staphylococcus aureus* and *Enterococci* obtained by 10 medical centers in all regions of Taiwan. MICs were determined using the agar dilution methods recommended by the Clinical and Laboratory Standards Institute (CLSI-M100-S18). The results are shown in the table below:

| | Compound 1 MIC (µg/mL) | | |
| --- | --- | --- | --- |
| Resistotype (No. of Isolates) | Range | MIC50 | MIC90 |
| Ciprofloxacin-susceptible MRSA (n = 20) | ≦0.03-0.06 | ≦0.03 | ≦0.03 |
| Ciprofloxacin-resistant MRSA (n = 20) | 0.5-1 | 0.5 | 1 |
| Vancomycin-intermediate MRSA (n = 50) | 0.03-8 | 0.5 | 2 |
| Daptomycin-nonsusceptible MRSA (n = 5) | 0.5-1 | 0.5 | 1 |
| Vancomycin-resistant *E. faecium* (n = 78) | 0.06-16 | 4 | 16 |

-continued

| | Compound 1 MIC (µg/mL) | | |
| --- | --- | --- | --- |
| Resistotype (No. of Isolates) | Range | MIC50 | MIC90 |
| Vancomycin-resistant *E. faecalis* (n = 34) | 0.12-8 | 4 | 4 |

As shown in the table, Compound 1 was effective in inhibiting the MRSA isolates that are Ciprofloxacin-resistant, Vancomycin-intermediate-resistant, and Daptomycin-nonsusceptible. It was also effective in inhibiting Vancomycin-resistant *Enterococcus faecium* and Vancomycin-resistant *Enterococcus faecalis*.

Inhibition of *Staphylococcal* Bacteria by Compound 1

Compound 1 was tested for its inhibitory effect against 26 Methicillin-resistant *Staphylococcus aureus* (MRSA) strains, 2 hetero-Vancomycin intermediate *Staphylococcus aureus* (hVISA) strains, 24 Vancomycin-intermediate *Staphylococcus aureus* (VISA) strains, 5 Vancomycin-resistant *Staphylococcus aureus* (VRSA) strains, and 31 quinolone-resistant Vancomycin-susceptibale MRSA strains with defined mutations in QRDR. These mutations were determined by sequencing analysis of the QRDR (gyrA, gyrB, grlA, and grlB). Efflux testing was performed by the reserpine method (Brenwald, et al., *Antimicrob. Agents Chemother.* 1998, 42: 2032-2035). MICs were determined using the agar dilution methods recommended by the Clinical and Laboratory Standards Institute (CLSI-M 100-S18) and are shown in the table below:

| | MRSA (26) | | | hVISA(2) + VISA (24) + VRSA (5) | | | Quinolone-resistant MRSA (31) | | |
| --- | --- | --- | --- | --- | --- | --- | --- | --- | --- |
| Drug | Range | $MIC_{50}$ | $MIC_{90}$ | Range | $MIC_{50}$ | $MIC_{90}$ | Range | $MIC_{50}$ | $MIC_{90}$ |
| Compound 1 | 0.016-0.06 | 0.03 | 0.06 | 0.06-2 | 1 | 2 | 0.5-4.0 | 1 | 2 |
| Ciproflox | 0.25-2 | 1 | 1 | 0.5->128 | 64 | >128 | 16->128 | 64 | >128 |
| Levoflox | 0.25-1 | 0.25 | 0.5 | 0.5->32 | 16 | 32 | 4->32 | 16 | 32 |
| Moxiflox | 0.03-0.25 | 0.06 | 0.06 | 0.06-8 | 4 | 8 | 1-8 | 4 | 8 |
| Vanco | 0.5-1 | 1 | 1 | 1->32 | 4 | 32 | 0.5-2 | 1 | 1 |
| Teico | 0.5-1 | 0.5 | 1 | 1-32 | 8 | 16 | 0.25-2 | 0.5 | 1 |
| Dapto | 0.5-1 | 1 | 1 | 0.12-4 | 1 | 2 | 0.12-1 | 0.25 | 0.25 |
| Linezolid | 2-4 | 4 | 4 | 0.5-2 | 1 | 1 | 0.25-1 | 1 | 1 |
| Tige | 0.12-0.5 | 0.25 | 0.5 | 0.06-0.5 | 0.25 | 0.5 | 0.12-0.5 | 0.12 | 0.25 |
| Quinu/dalfo | 0.25-1 | 0.5 | 0.5 | 0.12-0.5 | 0.5 | 0.5 | 0.25-0.5 | 0.5 | 0.5 |

Ciproflox: Ciprofloxacin
Levoflox: Levofloxacin
Moxiflox: Moxifloxacin
Vanco: Vancomycin
Teico: Teicoplanin
Dapto: Daptomycin
Tige: Tigecycline
Quinu/dalfo: Quinupristin/dalfopristin Compound 1 effectively inhibited *Staphylococcus aureus* isolates that are Methicillin-resistant, hetero-Vancomycin intermediate, Vancomycin-intermediate, and Vancomycin-resistant. It also effectively inhibited quinolone-resistant Vancomycin-susceptibale MRSA. It showed very low MICs (0.06-4 μg/ml) against these strains.

Among 31 MRSA quinolone-resistant strains, 5 strains carry QRDR mutations [GyrA (S84L), GrlA (S80F/Y), GrlB (L413S, E422K/N, D432N, E471K); GyrA (S84L), GrlA (S80F/Y), GyrB (R404L); GyrA (S84L), GrlA (S80F/Y); GyrA (S84L), GrlA (S80F/Y, E84V), GrlB (E422D) and GyrA (S84L), GrlA (S80F/Y, E84V/K/G or S108N)]. Compound 1-associated efflux was found among genotypes known to be associated with resistant development.

Inhibition of Gram-Positive Cocci by Compound 1

From January-December 2007, 12 hospitals across Canada submitted isolates from patients attending hospital clinics, emergency rooms, medical and surgical wards, and intensive care units. 7881 isolates (CANWARD 2007) were collected including 3473 gram-positive cocci. Susceptibility testing for Compound 1 and Levofloxacin was performed using the Clinical and Laboratory Standards Institute broth microdilution. $MIC_{50}$ and $MIC_{90}$ are shown below:

| Organism (# isolates) | Compound 1 $MIC_{50}/MIC_{90}$ | Levo $MIC_{50}/MIC_{90}$ |
|---|---|---|
| SPN-All (656) | 0.015/0.015 | 0.5/1 |
| PenS (519) | 0.015/0.015 | 0.5/1 |
| PenI (103) | 0.015/0.015 | 0.5/1 |
| PenR (34) | 0.015/0.03 | 0.5/2 |
| CipR (29) | 0.03/0.12 | 2/16 |
| MSSA (372) | 0.03/0.12 | 0.25/4 |
| CA-MRSA (23) | 0.25/0.5 | 4/8 |
| HA-MRSA (91) | 4/>4 | >32/>32 |
| MSSE (32) | 0.03/0.5 | 4/>32 |
| MRSE (9) | 2/2 | >32/>32 |
| *E. faecalis* (81) | 0.12/1 | 2/>32 |
| *VISA (12) | 1/2 | 32/>32 |
| *VRSA (7) | 2 | 32 |

SPN—*S. pneumoniae*,
MSSA—methicillin-susceptible *S. aureus*,
CA—community-associated,
HA—health care associated,
VISA—vancomycin-intermediate *S. aureus*,
VRSA—vancomycin-resistant *S. aureus*. + median MIC,
MSSE—methicillin-susceptible *Staphylococcus epidermidis*,
MRSE—methicillin-resistant *Staphylococcus epidermidis*
*Isolates obtained through the Network on Antimicrobial Resistance in *Staphylococcus aureus* (NARSA) program: supported under NIAID, NIH Contract No. N01-AI-95359.

Compound 1 was more active than Levofloxacin in inhibiting gram-positive cocci including MRSA, VISA, VRSA, MRSE, PenI-SPN, PenR-SPN, and CipR-SPN.

Inhibition of *Helicobacter pylori* by Compound 1

Compound 1, Ciprofloxacin, Levofloxacin, Moxifloxacin, and Gemifloxacin were tested for their inhibitory effect against 200 isolates of *H. pylori* obtained by 10 medical centers in all regions of Taiwan (2000-2007). MICs were determined using the agar dilution methods recommended by the Clinical and Laboratory Standards Institute (CLSI-M100-S18).

Among the 200 *H. pylori* isolates, 2%, 6%, 29%, 2%, and 2% of them were resistant to amoxicillin (MICs≧0.5 μg/mL), clarithormycin (MICs≧1 μg/mL, CLSI), metronidazole (MICs≧8 μg/mL), ciprofloxacin (MICs≧1 μg/mL), and levofloxan (MICs≧1 μg/mL), respectively. The MIC range, $MIC_{50}$, and $MIC_{90}$ of the five quinolone drugs tested are as follows:

| | MIC (mg/mL) | | |
|---|---|---|---|
| Agent | Range | MIC50 | MIC90 |
| Ciprofloxacin | 0.12-2 | 0.25 | 0.5 |
| Levofloxacin | 0.12-1 | 0.25 | 0.5 |
| Moxifloxacin | 0.12-4 | 0.25 | 0.5 |
| Gemifloxacin | ≦0.03-0.5 | 0.06 | 0.12 |
| Compound 1 | 0.06-1 | 0.06 | 0.25 |

Compound 1 effectively inhibited *H. pylori* isolates. The above table shows that Compound 1 was more effective in inhibiting the isolates of *H. pylori* than Ciprofloxacin, Levofloxacin, and Moxifloxacin, and comparable to Gemifloxacin.

Inhibition of Antibiotic-resistant Bacterial by Compound 1'

Compound 1', Ciprofloxacin, and Levofloxacin were tested for their inhibitory effect against methicillin-resistant *Staphylococcus aureus* and methicillin-resistant *Streptococcus pneumoniae* at various concentrations between 0.008 and 8 μg/ml on 10 different days. The *Staphylococcus aureus* and *Streptococcus pneumoniae* isolates were obtained by 10 medical centers in all regions of Taiwan. MICs were determined using the broth microdilution method. As shown in the table below, Compound 1' was also very effective in inhibiting *Staphylococcus aureus* and *Streptococcus pneumoniae*.

| | $MIC_{50}/MIC_{90}$ (μg/mL) | | |
|---|---|---|---|
| Organism | Comp. 1' | Ciprofloxacin | Levofloxacin |
| MRSA-CIP (R) | 1.0/1.0 | 64 | — |
| MRSA-CIP (S) | 0.03/0.06 | 0.5 | — |
| MRSP-Levo (R) | 0.25/1.0 | — | >128 |
| MRSP-Levo (S) | 0.03/0.06 | — | 16 |

MRSA-CIP (R): Clinical isolate of MRSA-ciprofloxacin resistant strain.
MRSA-CIP (S): Clinical isolate of MRSA-ciprofloxacin sensitive strain.
MRSP-Levo (R): Clinical isolate of Methicillin-resistant *S. pnemoniae* Levofloxacin resistant strain.
MRSP-Levo (S): Clinical isolate of Methicillin-resistant *S. pnemoniae* Levofloxacin sensitive strain.

As shown in the table above, Compound 1' was effective in inhibiting methicillin-resistant *Staphylococcus aureus* and *Streptococcus pneumoniae*.

Pharmacokinetic Assays

Blood samples were collected from each subject taking Compound 1 on day 10 at 0 hour (pre-dose) and 0.5, 1, 1.5, 2, 4, 6, 8, 12, 16 and 24 hours (post-dose). 5 mL of each sample was transferred to a heparin sodium tube and immediately placed on ice. Plasma was separated by centrifugation at approximately 4° C. and transferred to appropriately labeled polypropylene specimen containers (two tubes with 1-1.5 mL plasma/tube) and frozen at approximately −70° C. before use.

Prior to analysis of the blood samples, pharmacokinetic assays were validated. The details of the assay validation are listed in the table below.

| Analyte | Assay Type | LLOQ | Accuracy (% of bias) | Precision (% CV) |
|---|---|---|---|---|
| Compound 1 | in plasma | 5.0 ng/mL | −1.8~2.2% | 4.3~7.5% |

LLOQ: lower limit of quantitation (LLOQ)
CV: coefficient of variation (CV)

The pharmacokinetic assays of the blood samples were performed by Charles River Laboratories (Worcester, Mass.).

| Antibiotic | Regimen | $AUC_{0-24}$ (hr * μg/mL) | Protein Binding (%) | Free $AUC_{0-24}$ (hr * μg/mL) | MIC90 (μg/mL) | Free $AUC_{0-24}$/MIC90 ratios at steady state | | | | |
|---|---|---|---|---|---|---|---|---|---|---|
| | | | | | | 0.125 | 0.25 | 0.5 | 0.75 | 1 |
| Compound 1 | 500 mg q24 p.o. | 38.6 | 16 | 32.4 | | 259 | 130 | 65 | 43 | 32 |
| | 750 mg q24 p.o. | 58.4 | 16 | 49.1 | | 393 | 196 | 98 | 65 | 49 |
| | 1000 mg q24 p.o. | 74.8 | 16 | 62.9 | | 503 | 251 | 126 | 84 | 63 |

| Antibiotic | Regimen | $C_{max}$ (μg/mL) | Protein Binding (%) | Free $C_{max}$ (μg/mL) | MIC90 (μg/mL) | Free Cmax/MIC90 ratios at steady state | | | | |
|---|---|---|---|---|---|---|---|---|---|---|
| | | | | | | 0.125 | 0.25 | 0.5 | 0.75 | 1 |
| Compound 1 | 500 mg q24 p.o. | 5.56 | 16 | 4.7 | | 37 | 19 | 9 | 6 | 5 |
| | 750 mg q24 p.o. | 6.82 | 16 | 5.7 | | 46 | 23 | 11 | 8 | 6 |
| | 1000 mg q24 p.o. | 8.20 | 16 | 6.9 | | 55 | 28 | 14 | 9 | 7 |

$C_{max}$ (Peak concentration of Compound 1 in plasma) and $AUC_{0-24\,h}$ (Area under the plasma concentration-time curve from 0 to 24 hours post-dosing, calculated by linear/log trapezoidal method) were determined from the plasma concentration-time data using non-compartmental approaches (Win-Nonlin version 4.1, Pharsight Corporation, CA).

Protein binding was also measured as follows: Ultrafiltrate (UF) samples were obtained by centrifuging the above-mentioned compound 1-containing heparinized human plasma in molecular weight cutoff ultrafiltration devices (30,000 Da) at ~3000 rpm (30 min, ~37° C.). The UF samples (0.025 mL) were mixed with $O^{13}CD_3$-compound-1 ($OCH_3$ group in compound 1 was replaced with $O^{13}CD_3$ group to obtain $O^{13}CD_3$-compound-1) as an internal standard solution (~800 ng/mL, 0.050 mL), diluted by 20 folds, and analyzed by reverse-phase HPLC on a 3.5 micron C-18 column. Quantitation was obtained by the MRM (multiple reaction monitoring) method through positive ion Turbo-Ion Spray ionization. Ultrafiltrate standards were used to quantify the unbound drug in plasma quality control samples and unknown specimens. Non-specific protein binding (NSB) was measured (NSB=0.0415) and used as a correction factor to determine the final % protein bindings. The nominal range of quantitation for the analyte was 50 to 10,000 ng/mL. 0.400 mL aliquot of human plasma was used in the assay. Sample concentrations were determined by back-calculation using a weighted linear ($1/x^2$) regression of a calibration curve generated from spiked UF standards. Over the linear range, the inter-batch % CV for Compound 1 was 4.9% to 11.8%.

Shown in the table below are the $AUC_{0-24}$, $C_{max}$, and protein binding values of Compound 1 when the subjects took 500 mg, 750 mg, and 1000 mg per day. The free $C_{max}$ and free $AUC_{0-24}$ values shown in the table are those that have been corrected for plasma protein binding. Also shown in the table are the ratios of free $C_{max}$/MIC and free AUC/MIC, which are useful for prediction of clinical and microbiological outcome as well as bacterial resistance development. Free $C_{max}$/MIC greater than about 8 and free AUC/MIC greater than about 100 are preferred for antibiotic drugs.

Other Embodiments

All of the features disclosed in this specification may be combined in any combination. An alternative feature serving the same, equivalent, or similar purpose may replace each feature disclosed in this specification. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating infection caused by community-associated methicillin-resistant *Staphylococcus aureus*, comprising administering to a subject in need thereof an effective amount of a compound of the following formula:

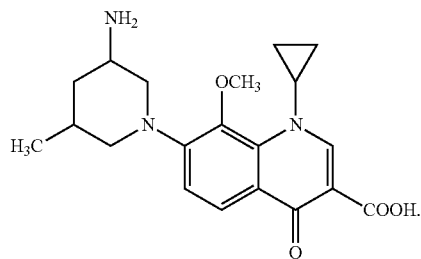

2. The method of claim 1, wherein the compound is in the salt form.

3. The method of claim 2, wherein the compound is in the malic acid salt form.

4. The method of claim 3, wherein the compound is in the malic acid salt hemihydrate form.

5. The method of claim 1, wherein the compound is

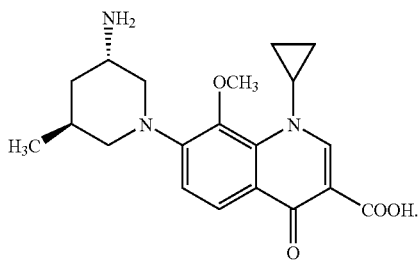

6. The method of claim 5, wherein the compound is in the salt form.

7. The method of claim 6, wherein the compound is in the malic acid salt form.

8. The method of claim 7, wherein the compound is in the malic acid salt hemihydrate form.

9. The method of claim 1, wherein the compound is

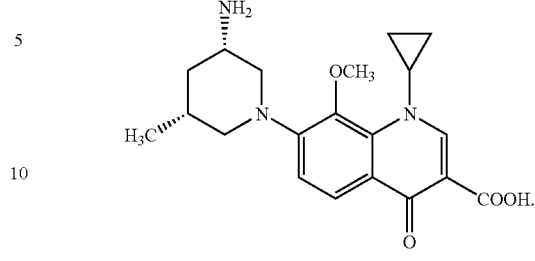

10. The method of claim 9, wherein the compound is in the salt form.

11. The method of claim 10, wherein the compound is in the malic acid salt form.

12. The method of claim 11, wherein the compound is in the malic acid salt hemihydrate form.

* * * * *